(12) United States Patent
Wong

(10) Patent No.: US 6,514,758 B2
(45) Date of Patent: Feb. 4, 2003

(54) METHODS FOR TREATMENT OF HIV AND OTHER INFECTIONS USING A T CELL OR VIRAL ACTIVATOR AND ANTI-RETROVIRAL COMBINATION THERAPY

(76) Inventor: Johnson T. Wong, 322 Far Reach Rd., Westwood, MA (US) 02090

( * ) Notice: Subject to any disclaimer, the term of this patent is extended or adjusted under 35 U.S.C. 154(b) by 0 days.

(21) Appl. No.: 10/100,432

(22) Filed: Mar. 18, 2002

(65) Prior Publication Data

US 2002/0094333 A1 Jul. 18, 2002

Related U.S. Application Data

(62) Division of application No. 09/199,890, filed on Nov. 24, 1998
(60) Provisional application No. 60/066,502, filed on Nov. 24, 1997.

(51) Int. Cl.[7] .............................. C12N 5/06; C12N 5/00; C12Q 1/70; G01N 33/53
(52) U.S. Cl. ......................... 435/335; 435/5; 435/7.24; 435/325; 435/334; 435/343.2
(58) Field of Search ........................... 435/5, 7.24, 325, 435/334, 335, 343.2

(56) References Cited

U.S. PATENT DOCUMENTS

| | | | |
|---|---|---|---|
| 4,361,549 A | 11/1982 | Kung et al. | 424/85 |
| 4,361,550 A | 11/1982 | Kung et al. | 424/85 |
| 4,363,799 A | 12/1982 | Kung et al. | 424/85 |
| 4,364,932 A | 12/1982 | Kung et al. | 424/85 |
| 4,364,933 A | 12/1982 | Kung et al. | 424/85 |
| 4,364,934 A | 12/1982 | Kung et al. | 424/85 |
| 4,364,935 A | 12/1982 | Kung et al. | 424/85 |
| 4,364,936 A | 12/1982 | Kung et al. | 424/85 |
| 4,364,937 A | 12/1982 | Kung et al. | 424/85 |
| 4,381,295 A | 4/1983 | Kung et al. | 424/85 |
| 4,542,225 A | 9/1985 | Blattler et al. | 548/473 |
| 4,925,648 A | 5/1990 | Hansen et al. | 424/1.1 |

FOREIGN PATENT DOCUMENTS

| | | |
|---|---|---|
| EP | 0 063 763 | 3/1986 |
| EP | 0 096 076 | 3/1986 |

OTHER PUBLICATIONS

Allison, J., "Structure, function, and serology of the T–cell antigen receptor complex" Annu. Rev. Immunol. 5:503–40, 1987.

Anderson et al., "Cross–linking of T3 (CD3) with T4 (CD4) enhances the proliferation of resting T lymphocytes" J. of Immunology 139(3):678–682, 1987.

Bank et al., "Perturbation of the T4 molecule transmits a negative signal to T cells" J. of Exper. Med. 162(4):1117–1408, 1985.

Bernard et al., "A novel human leukocyte differentiation antigen: monoclonal antibody anti–D44 defines . . . " J. of Immunology 132(5):2338–2344, 1984.

Caliendo et al., "Combination therapy for infection due to human immunodeficiency virus type 1" Clinical Infectious Diseases 18:516–24, 1994.

D'Aquila, R., "HIV–1 drug resistance" Clinics in Laboratory Medicine 14(2):393–422, 1994.

(List continued on next page.)

*Primary Examiner*—Hankyel T. Park
(74) *Attorney, Agent, or Firm*—Fish & Richardson P.C.

(57) ABSTRACT

Disclosed is a method for treating infection with a pathogen. The method involves administration of: (1) a substance which induces active pathogen replication in a cell latently infected with HIV and (2) an anti-pathogen drug. Also disclosed are methods for expanding CD4+ T cells from peripheral blood mononuclear cells isolated from human subjects in the presence of an antiretroviral drug and for treating HIV infection by infusing the expanded CD4+ cells into HIV-infected patients.

7 Claims, 5 Drawing Sheets

OTHER PUBLICATIONS

Emmrich et al., "Synergism in the activation of human CD8 T cells by cross–linking the T–cell receptor . . ." Proc. Nat'l. Acad. Sci. USA 83:8298–8302, 1986.

Finzi et al., "Identification of a reservoir for HIV–1 in patients on highly active antiretroviral therapy" Science 278:1295–1300, 1997.

Fleischer et al., "Function of the CD4 and CD8 molecules on human cytotoxic T lymphocytes: regulation . . . " J. of Immunology 136(5):1625–1628, 1986.

Kaye et al., "The Fab fragment of a directly activating monoclonal antibody that precipitates a disulfide–linked . . . " J. Exp. Med. 159:1397–1412, 1984.

Kellam et al., "Fifth mutation in human immunodeficiency virus type 1 reverse transcriptase contributes . . . " Proc. Nat'l. Acad. Sci. USA 89:1934–1938, 1992.

Kipps et al., "Importance of immunoglobulin isotype in human antibody–dependent, cell–mediated cytotoxicity directed . . . " J. Exp. Med. 161:1–17, 1985.

Landau et al., "The envelope glycoprotein of the human immunodeficiency virus binds to the immunoglobulin . . . " Nature 334(6178):159–162, 1988.

Larder et al., "Multiple mutations in HIV–1 reverse transcriptase confer high–level resistance to zidovudine (AZT)" Science 246:1089–1212, 1989.

Lazarovits et al., "Lymphocyte activation antigens" J. of Immunology 133(4):1857–1862, 1984.

Leontsini et al., "Physical and functional associate of the T cell receptor and the T3 molecular . . . ".

Levy, J., "Pathogenesis of human immunodeficiency virus infection" Microbiological Reviews 57(1):183–289, 1993.

Mason, D., "Effector mechanisms in allograft rejection" Ann. Rev. Immunol. 4:119–45, 1986.

Milstein et al., "Hybrid hybridomas and their use in immunohistochemistry" Nature 305:537–540, 1983.

Moretta et al., "Clonal heterogeneity in the requirement for T3, T4, and T8 molecules in human cytolytoc . . . " J. Exp. Med. 159:921–934, 1984.

Morimoto, et al., "The isolation and characterization of the human helper inducer T cell subset" J. of Immunology 134(6):3762–3769, 1985.

Parham, P., "In vitro production of a hybrid monoclonal antibody that preferentially binds to cells that . . . " Human Immunology 12:213–221, 1985.

Perenz et al., "Specific targeting of human peripheral bloot T cells by heteroaggregates containing . . . " J. of Exp. Med. 163:166–178, 1986.

Reinherz et al., "Subpopulations of the T4 inducer T cell subset in man: Evidence for an amplifier . . . " J. of Immunology 126(1):67–70, 1981.

Rosenberg et al., "The immunopathogenesis of HIV infection" Advances in Immunology 47:377–431, 1989.

Sattentau et al., "Epitopes of the CD4 antigen and HIV infection" Science 234(4780)L1048–1123, 1986.

Schinazi et al., "Mutations in HIV–1 reverse trasncriptase and protease associated with drug resistance" Int'l. Antiviral News 2(5):72–75, 1994.

Shaw et al., "Susceptibility of cytotoxic T lymphocyte (CTL) clones to inhibition by anti–T3 and anti–T4 . . . " J. of Immunology 134(5):3019–3026, 1985.

Shearer et al., "Early T–helper cell defects in HIV infection" AIDS 5(3):245–253, 1991.

Staerz et al., "Hybrid hybridoma producing a bispecific monoclonal antibody that can focus effector T–cell activity" Proc. Nat'l. Acad. Sci. USA 83:1453–1457, 1986.

St. Clair et al., "Resistance to ddI and sensitivity to AZT induced by a mutation in HIV–1 reverse transcriptase" Science 253:1457–1612, 1991.

Terasai et al., "Microdroplet testing for HLA–A, –B, –C, and –D antigens" Amer. J. of Clinical Pathology 69:103–20, 1978.

Van Wauwe et al., "OKT3: A monoclonal anti–human T lumphocyte antibody with potent mitogenic properties" J. of Immunology 124(5):2708–2713, 1980.

Walker et al., "Activation of T cells by cross–linking an anti–CD3 antibody with a second anti–T cell . . . " Eur. J. Immunol. 17:873–880, 1987.

Wong et al., "Recovery of replication–competent HIV despite prolonged suppression of plasma viremia" Science 278:1291–1295, 1997.

Wong et al., "Bi–specific monoclonal antibodies: selective binding and complement fixation to cells . . . " J. of Immunology 139(4):1369–1374, 1987.

Wong et al., "Bi–specific monoclonal antibodies (BSMAB): selective destruction and proliferation . . . " Federation of Amer. Soc. for Exp. Biology, 72nd Annual Meeting, Abstract #8898, 1988.

Wong et al., "Bi–specific monoclonal antibody (BSMA): production by fusion of pre–existing hybridomas . . . " J. of Allergy and Clinical Immunology, 42nd Annual Meeting, Abstract #434, 1986.

Wilson et al., "Ex Vivo Expansion of CD4 Lymphocytes from Human Immunodeficiency Virus Type–1 Infected Persons . . . " JID 172:88–96, 1995.

HIV-1 infected subject characteristics and maximum CD4+ T cell expansion

| Subject | Age Ethnic Sex Preference | Duration since +HIV serology (yr) | Clinical Status | Therapy | CD4+ T cell count at time of test | Viral load | Total cell number<br><br>Maximum CD4+ T cell expansion<br><br>(Avg. No. of division per cell) |
|---|---|---|---|---|---|---|---|
| 161j | 40 Caucasian Male Hemophiliac | 16 | LONG TERM NON-PROGRESSOR | None | 1440 | <400 | $3 \times 10^{18}$<br><br>$3 \times 10^{11}$ fold<br><br>(38) |
| 01141g | 35 Caucasian Male Homosexual | 12 | Asymptomatic | D4T | 400 | ND | $\geq 10^{12}$<br><br>$\geq 10^5$ fold<br><br>($\geq 16.7$) |
| 011436 | 33 Caucasian Male Homosexual | 7 | Asymptomatic | AZT±ddI or ddC | 350 | ND | $\geq 3 \times 10^{14}$<br><br>$\geq 3 \times 10^7$ fold<br><br>($\geq 25$) |
| SB | 30 Puerto Rican Male Homosexual | 7 | Asymptomatic | AZT,3TC, Indinavir started 3wk before test | 300 | 132,000 before drug <400 during Rx | $10^{13}$<br><br>$10^5$ fold<br><br>(16.7) |
| 011430j | 75 Caucasian Male Bisexual | 7 | Asymptomatic | AZT,3TC | 300 | 21,252 | $10^{10}$<br><br>$10^3$ fold<br><br>(10) |
| 012215e | 34 Caucasian Male Homosexual | 5 | Oral candidiasis, Oral hairy leukoplakia, Scrotal molluscums | None anti-retroviral naive | 170 | 212,000 | $2.2 \times 10^{10}$<br><br>$4 \times 10^3$ fold<br><br>(12) |
| Mean number of division per cell of the six HIV-1 infected subjects studied. | | | | | | | 19.7±10.3 |
| Mean number of division per cell among SB, 011430j, and 012215e | | | | | | | 12.9±3.4 |

FIG. 4

HIV-1 p24 antigen production during expansion of CD4 lymphocytes using CD3,8 bispecific monoclonal antibody from 12 HIV-infected persons in the presence or absence of zidovudine, didanosine, and pyridinone combination treatment.

| Subject (no. of CD4 cells/mm³) | Treatment | \multicolumn{7}{c}{p24 antigen (ng/mL) at week} | | | | | | |
|---|---|---|---|---|---|---|---|---|
| | | 1 | 2 | 3 | 4 | 6 | 8 | 10-16 (day) |
| A (30) | − | 2.7 | 36.0 | 8.8 | 1.9 | | | |
| B (30) | + | <0.005 | <0.005 | <0.005 | <0.005 | <0.005 | <0.005 | |
| | − | 4.0 | 25.0 | 64.0 | 66.0 | | | |
| | + | 0.005 | <0.005 | <0.005 | <0.005 | <0.005 | <0.005 | <0.005 (120) |
| C (30) | − | 16.0 | 41.0 | 18.6 | 25.0 | | | |
| | + | 0.02 | <0.005 | <0.005 | <0.005 | | | |
| D (147) | − | 9.3* | 33.0 | 14.0 | | | | |
| | + | 3.3* | 15.6 | 60.0 | | | | |
| E (220) | − | 0.016 | 91.0 | 24.0 | 3.0 | | | |
| | + | 0.005 | <0.005 | <0.005 | <0.005 | <0.005 | <0.005 | <0.005 (107) |
| F (316) | − | 0.1 | 0.68 | 179.0 | 320.0 | | | |
| | + | 0.035 | 0.1 | 2.4 | 111.0 | | | |
| G (330) | − | 0.04 | 88.0 | 97.0 | 83.0 | | | |
| | + | 0.008 | <0.005 | <0.005 | <0.005 | <0.005 | <0.005 | <0.005 (85) |
| H (330) | − | <0.005 | 4.3 | 174.0 | 20.0 | | | |
| | + | <0.005 | <0.005 | <0.005 | <0.005 | <0.005 | <0.005 | <0.005 (96) |
| J (350) | − | 0.023 | 3.1 | 116.0 | 97.0 | | | |
| | + | <0.005 | <0.005 | <0.005 | <0.005 | <0.005 | <0.005 | <0.005 (120) |
| K (370) | − | 0.1 | 175.0 | 176.0 | 12.0 | | | |
| | + | 0.055 | 0.028 | <0.005 | <0.005 | <0.005 | 0.048 | 173.0 (75) |
| L (400) | − | 0.011 | 1.8 | 93.0 | 280.0 | | | |
| | + | <0.005 | <0.005 | <0.005 | <0.005 | <0.005 | <0.005 | <0.005 (121) |
| M (550) | − | <0.005 | <0.005 | 0.26 | 24.0 | | | |
| | + | 0.005 | <0.005 | <0.005 | <0.005 | <0.005 | <0.005 | <0.005 (120) |

NOTE. Cultures were restimulated at 10- to 14-day intervals with anti-CD3 monoclonal antibodies and irradiated donor peripheral blood mononuclear cells. Cell-free supernatants were obtained twice weekly and tested for p24 antigen. Cultures determined to be HIV-infected were terminated at 3-4 weeks. −, not treated; +, treated.
* Supernatant from day 10.

FIG. 5

METHODS FOR TREATMENT OF HIV AND OTHER INFECTIONS USING A T CELL OR VIRAL ACTIVATOR AND ANTI-RETROVIRAL COMBINATION THERAPY

RELATED APPLICATION INFORMATION

This application is a divisional of application Ser. No. 09/199,890, filed Nov. 24, 1998, which claims priority from provisional application serial No. 60/066,502, filed Nov. 24, 1997.

FIELD OF THE INVENTION

The invention relates to the treatment of Human Immunodeficiency Virus (HIV) infection and other infections.

BACKGROUND OF THE INVENTION

HIV infection leads to progressive deterioration of the immune system in most infected subjects. This infection frequently leads to an immune system dysfunction which may culminate in AIDS, a syndrome characterized by the development of opportunistic infections and cancer (Levy, 1993, Microbiol. Rev., 57:183–289). Cells infected with HIV include, e.g., CD4+ T cells, macrophages/monocytes, dendritic cells, and glial cells. The immune system in late stages of AIDS is severely compromised due to loss or dysfunction of CD4+ T cells (Shearer et al., 1991, AIDS, 5:245–53), macrophages, monocytes and dendritic cells. (Rosenberg et al., 1989, Adv. Immunol., 46:377).

Anti-retroviral drugs, such as reverse transcriptase inhibitors, viral protease inhibitors, and viral entry inhibitors have been used to treat HIV infection. (Caliendo et al., 1994, Clin. Infect. Dis., 18:516–24). These treatments can effectively suppress viral production when used in combinations known as HAART (highly active anti-retroviral therapy). However, they are mainly effective in preventing new infection of uninfected cells. They are generally far less effective in eliminating latent virus from infected cells. Even after two years on HAART, HIV-1 can still be induced, and viral production resume when HAART is stopped (Finzi et al., 1997, Science, 278:1295–1300; Wong et al., 1997, Science, 278:1291–1295). Hence, HAART likely needs to be continued indefinitely. This poses significant difficulties. HAART regimens have many side effects, are difficult to comply with, and are expensive. Moreover, prolonged treatment with these drugs often leads to the emergence of drug resistant viral strains (Larder et al., 1989, Science, 246:1155–8; Kellam et al., 1992, Proc. Nat'l. Acad. Sci. USA, 89:1934–8; St. Clair et al., 1991, Science, 253:1557–9). Combination therapies entailing treatment with two or more drugs which attack different points in the HIV replication cycle delay the emergence of resistant HIV strains. (D'Aquila, 1994, Clin. Lab. Med., 14:393:422). However, recent data suggest that HIV strains having multi-drug resistance may eventually develop in a significant portion of patients treated with combination therapy. (Schinazi et al., 1994, Int. Antiviral News, 2:72–5).

Many other important infectious pathogens can exist in a latent state where they are dormant or replicate very slowly. Examples of these pathogens include retroviruses, e.g., human immunodeficiency virus type 2 (HIV-2), human T lymphotropic virus type 2 (HTLV-2); herpesviruses, e.g., Epstein-Barr virus (EBV), cytomegalovirus (CMV), herpes simplex type 1 (HSV-1), herpes simplex type 2 (HSV-2), herpes zoster virus (HZV), herpes virus type 6 (HHV-6), herpes virus type 7 (HHV-7); hepatitis viruses, e.g., hepatitis B (HBV), hepatitis C (HCV), the delta agent, and hepatitis E, mycobacteria, e.g., M. tuberculosis (MTB), M. avium (MA), M. Leprae; and fungal agents e.g., histoplasmosis, coccidiomycosis, cryptococcus, and pneumocystis. Keeping the infectious pathogen in latency is desirable when there is no available therapy. However, in many cases, the pathogen is not completely latent and therapy is required. Unfortunately, while active infection can often be contained by therapy, it is difficult or impossible to attack latent pathogen. Moreover, latent infection can give rise to renewed production of the infectious microbes when the anti-viral/anti-microbial agents are stopped.

HIV-2 can cause immunodeficiency similar to HIV-1. HTLV-1 has been shown to cause T cell lymphoma. EBV may cause lymphoma and other lymphoproliferative diseases. CMV may cause retinitis, hepatitis, pneumonitis, and other systemic illness, especially in immunocompromised host. HSV 1 and 2, and Herpes Zoster (HZV) can cause painful vesicles at the area of infection and occasional meningitis. HHV-6 has been demonstrated to be present in and may contribute to the pathogenesis in certain subgroups of patients with multiple sclerosis and chronic fatigue syndrome. Nucleoside analogs such as ganiclovir, famciclovir, lamivudine, and ribavirin have been shown to be effective against many of these infections. These drugs interfere with viral replication, but they generally cannot attack latent virus. Hence, viral replication often resumes when the drugs are withdrawn.

SUMMARY OF THE INVENTION

The invention features a method for treating HIV infection and other infections. The method entails the administration of: (1) a substance which induces active pathogen replication in a cell latently infected with the pathogen and (2) an anti-pathogen drug.

In a preferred embodiment the invention features a method for treating retroviral, e.g., HIV-1 infection, by administering: (1) a substance which induces active viral replication in a latently infected cell and (2) an anti-retroviral drug.

The substance used to induce active viral replication is generally a substance which induces the activation or proliferation of the latently infected cell, e.g., a T cell, or is substance capable of inducing viral replication. Mitogenic lectins, such as phytohemagglutinins, can induce the activation or proliferation of human T cells. Similarly, polyclonal or monoclonal antibodies capable of binding T cell surface molecules such as, e.g., α, β or γ, 67 T cell receptors, CD3, CD2, CD4, CD8, CD28, Thy-1, can often induce T cell activation or proliferation. Additionally, bispecific monoclonal antibodies capable of binding more than one antigen can be used. For example, a bispecific monoclonal antibody (BSMAB) having specificity for both CD3 and CD8, (CD3, 8 BSMAB) can induce activation and proliferation of CD4+ T cells. (Wong et al., 1987, J. Immunol., 139:1369–74; Wong et al., 1989, J. Immunol. 143:3403–11, U.S. Pat. No. 5,601,819, all incorporated herein by reference).

Substances that can activate viral replication directly include: cytokines such as TNF-α and other stimulators of NFκB activity, analogs or fragments of cytokines such as IL-1 and IL-2 and IL-7, and transactivators encoded by various sequences from various virus, e.g., herpes virus (HSV, EBV, CMV, HHV-6), HTLV-1, and HBV.

The anti-retroviral drug used in the methods of the invention can be any substance which can inhibit, reduce or eliminate retroviral infection of a cell. Commonly used anti-retroviral drugs include reverse transcriptase inhibitors, protease inhibitors, and inhibitors of viral entry. Reverse transcriptase inhibitors can be nucleoside analogues, e.g., AZT (Zidovudine; Glaxo-Burroughs Wellcome Co., Research Triangle Park, N.C.), ddI (Didanosine; Bristol-Myers Squibb; Wallingford, Conn.), 3TC (Glaxo-Burroughs Wellcome), d4T (Stavudine; Bristol-Myers Squibb), or ddC (Zalcitabine; Hoffman-La Roche; Basel, Switzerland); or non-nucleoside drugs, e.g., Nevirapine (Viramune; Roxane Laboratories; Columbus, Ohio), Delaviridine (Rescriptor; Pharmacia & Upjohn; Kalamazoo, Mich.), Abacavir or Pyridnone (Merck, Sharp & Dohme; Rahway, N.J.). Protease inhibitors which can be used include, e.g., Indinavir (Crixivan; Merck; West Point, Pa.), Ritonavir (Novir; Abbott Laboratories; Abbott Park, Ill.), Saquinavir (Invirase; Roche; Palo Alto, Calif.), Nelfinavir (Agouron Pharmaceuticals; La Jolla, Calif.), and Amprenavir.

The invention also features a method of treating a patient infected with HIV, comprising administering to the patient either (a) an amount of a CD4+ T cell mitogen sufficient to induce activation of CD4+ T cells and replication of HIV within latently infected CD4+ T cells in combination with a therapeutically effective amount of at least one, but preferably more than one, anti-retroviral drug, (b) or a direct virus activator in combination with a therapeutically effective amount of at least one, but preferably more than one, anti-retroviral drug.

The invention also features an ex vivo method of expanding CD4+ T cells from a sample of peripheral blood mononuclear cells (PBMCs) isolated from a human. CD4+ T cells are expanded by culturing PBMCs in an artificial capillary cell culture system in the presence of an amount of a CD4+ T cell mitogen, e.g., CD3, 8 BSMAB sufficient to induce activation of CD4+ T cells and replication of HIV within latently infected CD4+ T cells. The invention also features an ex vivo method of expanding CD4+ T cells from a sample of peripheral blood mononuclear cells isolated from a human, comprising culturing the peripheral blood mononuclear cells in an artificial capillary cell culture system in the presence of a T cell mitogen and at least one anti-retroviral drug.

The invention also features a method of treating an HIV-infected patient by administering to the patient the CD4+ cells grown ex vivo. By the methods described above, CD4+ T cells taken from the patient can be expanded ex vivo to sufficient quantity to transfuse back into the patient.

The invention also features a method of treating a patient infected with HTLV, comprising administering to the patient an amount of either (a) a CD4+ T cell mitogen sufficient to induce activation of CD4+ T cells and replication of HTLV within latently infected CD4+ T cells and a therapeutically effective amount of at least one, but preferably more than one, anti-retroviral drug or (b) a direct virus activator and with a therapeutically effective amount of at least one, but preferably more than one, anti-retroviral drug. Anti-retroviral drugs can include reverse transcriptase inhibitors, viral protease inhibitors, and viral entry inhibitors (e.g., fragments of viral entry receptors or co-receptors).

The invention also features a method of treating a patient infected with members of the herpesvirus family such as EBV, CMX, HSV type 1, HSV type 2, HHV-6 and HHV-7, comprising administering to the patient an amount of either (a) a cellular mitogen sufficient to induce activation of the latently infected cells and replication of the virus within the infected cells and therapeutically effective amount of at least one, but preferably more than one, antiviral drug or (b) a direct virus activator and a therapeutically effective amount of at least one, but preferably more than one, anti-viral drug. The cellular mitogen may include PHA for all cell types, pokeweed mitogen for B cells (EBV), LPS (lipopolysaccharide) for monocytes/macrophages, anti-CD3/TCR for T cells. Viral activators, some of which may be cellular activators, include IL-6, TNF-α, and GM-CSF. Anti-viral drugs effective against the herpesvirus family include Acyclovir (Glaxo Wellcome), Ganiciclovir (Roche Laboratories), and Famciclovir (SmithKline Beecham).

The invention also features a method of treating a patient infected with a hepatitis virus that causes chronic diseases such as hepatitis B, hepatitis C, delta agent, and hepatitis E, comprising administering to the patient an amount of either: (a) a cellular mitogen sufficient to induce activation of the latently infected cells and replication of the virus within the infected cells and therapeutically effective amount of at least one, but preferably more than one, anti-viral drug, or (b) a direct virus activator and a therapeutically effective amount of at least one, but preferably more than one, anti-viral drug. The cellular mitogens include PHA for all cell types, LPS (liposaccharide) for monocytes/macrophages, and anti-CD3/TCR for T cells. Viral activators, some of which may be cellular activators, include IL-6, IFN-γ, and TNF-α. Anti-viral drugs affective against the hepatitis viruses include: Lamivudine (Glaxo Wellcome), Ganciclovir (Roche Laboratories), Faciclovir (SmithKline Beecham), and IFN-α, (SmithKline Beecham).

The invention also features a method of treating a patient infected with a pathogen that has a latent state, e.g., infection with a mycobacteria, the method comprising administering to the patient either (a) an amount of cellular mitogen sufficient to induce activation of the latently infected cells and replication of the infectious pathogen and a therapeutically effective amount of at least one, but preferably more than one, anti-infection drug or (b) a direct activator of the infectious pathogen and a therapeutically effective amount of at least one, but preferably more than one, anti-infection drug. Suitable cellular mitogens include: PHA for all cell types, LPS (liposaccharide) for monocytes/macrophages, and anti-CD3/TCR for T cells. Activators include corticosteroid, TNF-α, and IL-2. In some cases, activators of the microorganism may also act as cellular activators. Drugs which may be used to treat mycobacterial infection include isoniazid, rifampin, clarithromycin, and ethambutol.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In the case of conflict, the present document, including definitions, will control. Unless otherwise indicated, materials, methods, and examples described herein are illustrative only and not intended to be limiting.

Various features of the invention will be apparent from the following detailed description and from the claims.

BRIEF DESCRIPTION OF THE DRAWINGS

FIG. 4 is a table of HIV-1 infected subject characteristics and maximum CD4+ T cell expansion.

FIG. 5 is a table of HIV-1 p24 antigen production.

DESCRIPTION OF THE PREFERRED EMBODIMENTS

Figure 1:
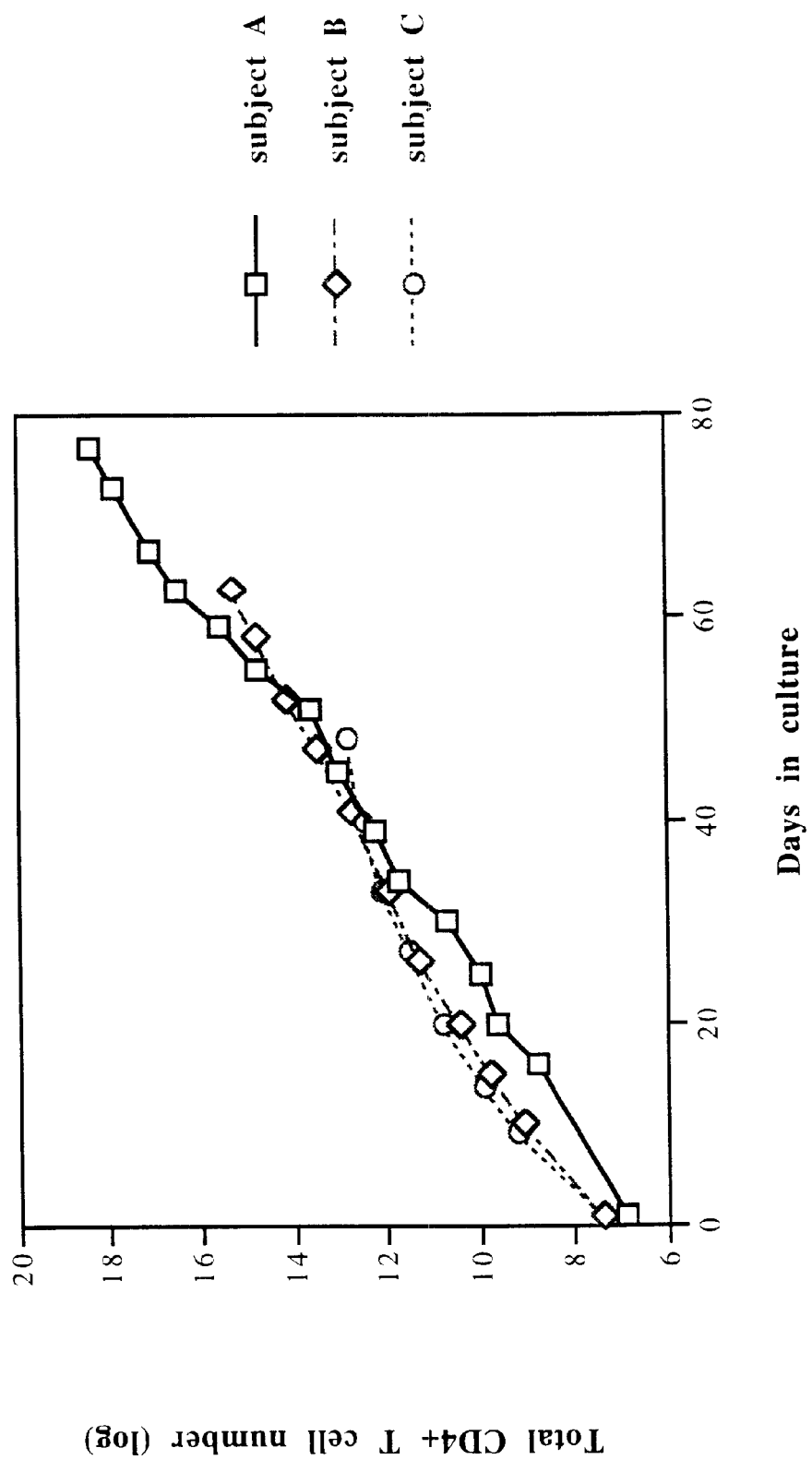
FIG. 1 is a graph depicting proliferation of CD4+ T cells induced by culturing PBMCs isolated from non-HIV infected subjects in the presence of CD3, 8 BSMAB and IL-2.

The invention is directed to a method of treating infection with a pathogen by administering a compound which provides a strong activation stimulus that activates all or nearly all the pathogen from the latent state and concurrently administering one or more anti-pathogen drugs that can inhibit pathogen replication or viability. Under these conditions, infected cells are killed by the replicating pathogen but infection of uninfected cells is largely prevented by the anti-pathogen drug. Thus, by inducing the death of latently infected cells, the method of the invention can substantially reduce the reservoir of latently-infected cells present in the patient.

The invention is directed to a method of treating HIV infection by administering a compound which provides a strong activation stimulus that activates all or nearly all the virus from the latent state and concurrently administering one or more anti-retroviral drugs that can inhibit viral replication. Under these conditions, infected cells are killed by the replicating virus but infection of uninfected cells is largely prevented by the anti-retroviral drugs. Any viruses remaining extracellularly are rapidly degraded because HIV is unstable in the fluid phase. Thus, by inducing the death of latently infected cells, the method of the invention can substantially reduce the reservoir of latently-infected cells present in the patient.

HIV replication in latently infected CD4+ T cells can be induced by activating the cells. Similarly, HIV in latently infected macrophages or monocytes can be activated by the cytokines such as tumor necrosis factor (TNF-α) that are released by activated T cells. The concurrent presence of the cell stimulus and anti-retroviral therapy is important because activation in the absence of anti-retroviral therapy potentially can lead to acceleration of the infection.

Concurrent In Vivo Administration of a T Cell Mitogen and One or More Anti-retroviral Drugs to an HIV-infected Subject HIV-infected subjects are treated with a therapeutically effective amount of a T cell mitogen and at least one anti-retroviral drug. Those skilled in the art can select an appropriate therapeutic regime employing one or more anti-retroviral drugs. For example, combinations and dosages of anti-retroviral drugs can be determined from published recommendations (Carpenter et al., 1997, Anti-retroviral Therapy for HIV Infection in 1997-Updated Recommendations of the International AIDS Society-USA Panel, J. American Medical Assoc., 277:1962). Suitable T cell mitogens include any substance which has the ability to activate T cells or cause their proliferation. For example, mitogenic lectins (e.g., PHA), mitogenic antibodies, (e.g., anti-CD3 specific antibodies), mitogenic bispecific antibodies (e.g., CD3, 8 BSMAB), lymphokines (e.g., IL-2) and cytokines (e.g., TNF-α). Appropriate dosages of T cell mitogens to be administered to an HIV-infected person can be determined by one skilled in the art. For example, concentrations of T cell mitogens known to cause the proliferation of T cells in vitro, can be extrapolated to determine the dosage required to generate in vivo T cell activation or proliferation.

For example, 0.02–0.2 μg/ml of CD3, 8 BSMAB causes T cell proliferation in an in vitro assay. Accordingly, CD3, 8 BSMAB can be administered at, e.g., 4 to 40 mg/kg/day to a human subject for approximately, e.g., 3–7 days until the subject's plasma concentration of CD3, 8 BSMAB is between 0.02–0.2 μg/ml. Similarly, the dose of T cell mitogen necessary to achieve T cell activation or proliferation in a human subject can be extrapolated from data obtained from animal experiments. The dose of T cell mitogen should be sufficient to induce activation of CD4+ T cells and replication of HIV within latently infected T cells.

In one embodiment, HIV-infected subjects are treated with: (1) a combination of AZT (zidovudine) 200 mg 3×/day, 3TC (lamivudine) 150 mg 2×/day, and Indinavir 800 mg/day for a minimum of one week; (2) CD3, 8 BSMAB at 4–40 μg/kg/day for 3 to 7 days (until plasma level is 0.02–0.2 μg/ml); and (3) IL-2 at $10^6$ units/m$^2$ daily for one month. The dosage of IL-2 is then decreased gradually to zero over two months to three months. Of course, the T cell mitogen and the anti-retroviral drugs need not be co-administered. However, a therapeutic amount of the anti-retroviral drugs should be present during stimulation or T cell proliferation.

Throughout the treatment, the subjects can be monitored for adverse effects of the treatment protocol, e.g., vital signs, liver enzymes, renal function, and glucose levels. T cell activation can be assessed by CBC with differential, IL-2 receptor or HLA-DR expression. Patient blood samples can be tested for HIV by several methods known to those skilled in the art. For example, levels of anti-HIV antibody and viral proteins can be determined by standard commercial kits (e.g., ELISA or RIA). Polymerase chain reaction (PCR) can be used to assess the presence of HIV nucleic acid in biological samples. PBMCs can be harvested from the treated subjects at two week intervals and tested for infectious HIV by co-culturing with known non-infected CD4+ cells. Infection of previously non-infected cells would indicate that infectious HIV was present in the subject. The foregoing assays can also be used to test lymph node samples from the subject for infectious HIV.

Ex Vivo Expansion of CD4+ T Cells from PBMCs Isolated from Human Subjects

CD4+ T cells can be expanded from a sample of PBMCs isolated from an HIV-infected or non-HIV infected subjects according to the method of Wilson et al. (1995, J. Infect. Dis., 172:88–96). PBMCs can be isolated from a human by methods well known in the art. For example, a sample of blood can be removed from a human via a syringe and needle and placed into a container containing anticoagulants. PBMCs can be isolated by centrifuging the sample through a ficoll diatrizoate gradient (Sigma, St. Louis, Mo.).

CD4+ T cells can also be expanded from a sample of PBMCs isolated from an HIV-infected or non-HIV infected subject using an artificial capillary system (Knazek et al, 1972, Science, 178:65–67; Bresler et al., 1993, Repetitive Expansion of Large Numbers of CD8+ Lymphocytes within an Artificial Capillary System, Abstract/AAI & CIS Conjoined Annual Meeting). Artificial capillary systems are available commercially, e.g., CELLMAX® artificial capillary system (Cellco, Inc., Germantown, Md.).

In one embodiment of the invention, the CELLMAX® artificial capillary culture system (Cellco) is primed by pre-infusion for 24–72 hours with 100 ml of Cellgro Complete Serum Free Medium (Mediatech) supplemented with 1% human AB serum (Sigma), gentamicin (Gibco) 50 μg/ml, and cefoxitin (Merck) 50 μg/ml (designated complete medium). The antibiotics are used to inhibit bacterial growth should the rare contamination occur. On day zero, $3-5\times10^7$ PBMC (only a fraction of which will be CD4+ T cells) are suspended in 12 ml of complete medium supplemented with rIL-2 (Hoffman-LaRoche) 100 U/ml and CD3, 8 BSMAB 6 μg/ml. The triple anti-retroviral combination of either (a) AZT (Zidovudine, Glaxo-Burroughs Wellcome Co.) 1 μM+ddI (Didanosine, Bristol-Myers Squibb) 10 μM+nevirapine 0.1 μM or (b) AZT+3TC (Glaxo-Burroughs Wellcome Co.)+Indinavir (Merck) 0.4 μM are added. Other combinations can be selected based on analysis of the drug resistance pattern determined in screening plate cultures.

The cell suspension is then inoculated directly into the extracapillary space (ECS) of the Cellmax artificial capillary culture cartridge. Next, 150 ml of the complete medium, supplemented with the IL-2 and the triple anti-retroviral agents, is added to the feeding reservoir. The whole system is then placed into a designated incubator set at 37° C. and 5% $CO_2$. Perfusion rate is set at 50 ml/min for the first 7–10 days of culture. On day 3, the CD3, 8 BSMAB is largely removed from the ECS of the cartridge by replacing 10 ml of the ECS medium with the IL-2 /triple anti-retroviral drug supplemented complete medium.

The rate and cell growth and consumption of nutrient is followed by measuring the glucose consumption with the Accu-Chek Advantage glucometer (Boehringer Mannheim) after diluting the medium 1:1 with PBS. When the glucose concentration drops to approximately 100–150 mg/dl, the feeding medium in the reservoir bottle is increased to 300 ml. With the next equivalent drop in glucose, the reservoir medium is increased to 500 ml and the perfusion rate increased to 100 ml/min. At day 21 (or day 19), the feeding medium is changed to complete medium supplemented with IL-2 but without anti-retroviral drugs. When the glucose concentration again drops to 150 mg/dl (at the 500 ml stage), the cells are harvested and counted. During the harvest, ¾ to ⅞ of the cells are removed by 3–4 successive vigorous washes, leaving ¼ to ⅛ of the cells in the cartridge. Approximately $0.8-1.8\times10^9$ cells are removed by each harvest. The remaining cells are fed with new IL-2 -supplemented complete medium and be allowed to grow.

Repeated harvesting can be performed with every other exchange of the 500 ml feeding medium until the cultured cells no longer grow (defined as decreasing number of viable cells for more than two weeks) or when the total numbers of CD4+ T cells generated has reached $10^{21}$ cells (the equivalent of approximately 47 divisions).

Expansion for each harvest is calculated by the total number of CD4+ T cells in the cartridge at the time of harvest (number of cells removed+the calculated number of cells remaining in the cartridge [estimated by the 12 ml volume of the ECS×cell concentration of the last wash volume])/starting number of CD4+ T cells. The total cell expansion is calculated by the multiplying the fold expansion of each harvest. The total number of expanded cells is then calculated by multiplying the total number of cells after expansion by the number of CD4+ T cells at the initiation of culture. Cells removed during harvest can be phenotypically typed and/or frozen in $10\times10^6$ cell aliquots in, for example, liquid nitrogen, after each harvest.

The frozen cells can be thawed in batches for immunobiological assays. The ECS supernatant removed during the cell harvest can also be frozen and thawed for batched p24 assays. Collected supernatants are diluted by the addition of 1/10 volume of 5% Triton X-100 (DuPont), and stored at −20° C. until run using a standard DuPont enzyme-linked immunoabsorbent assay (ELISA) kit for the detection of HIV-1 p24 antigen. Samples from individual subjects can be stored and run in batches. A standard curve can be generated in each assay, and those values which exceeded the reactive threshold of 0.05 plus the mean optical density of the negative controls (equivalent to 4 standard deviations above the mean) are considered to be positive.

Treatment of HIV-infected Patients with Ex Vivo Expanded CD4+ T Cells

For infusion of ex vivo expanded CD4+ cells, PBMCs can be isolated from a human subject and expanded as described above. The expanded CD4+ cells can be removed from cell culture, washed free of medium, placed in a pharmaceutically acceptable carrier (e.g. sterile saline, human serum, or human blood), and infused into the subject intravenously by methods known in the art. Preferably, the PBMCs to be cultured for expansion in to CD4+ T cells are autologous to the subject to be infused.

Administration of CD3, 8 BSMAB to PBMCs Isolated from HIV-infected Patients

In the absence of anti-retroviral drugs, the addition of a high concentration of CD3, 8 BSMAB in the presence of IL-2 to a culture of PBMCs isolated from HIV-infected subjects led to the depletion of CD8+ T cells and an expansion of CD4+ T cells. The percent of CD8+ cells in the culture increased with lower concentrations of CD3, 8 BSMAB. At concentrations between 0.2–2.0 μg/ml, there was a net increase in both CD4+ T cells and CD8+ T cells, with greater expansion of the CD4+ T cells. In comparison, in response to CD3, 8 BSMAB alone, the CD4+ T cells were activated to proliferate and express CD25 (interleukin-2 receptor). The stimulation of the PBMCs in this manner turn leads to a massive increase in HIV replication, as measured by the marked elevation of p24 HIV protein levels in the harvested tissue culture supernatant (FIG. 5). Absent anti-retroviral drugs, this massive activation of HIV will eventually cause a sharp decrease in the CD4+ T cell population.

Adding phytohemagglutinin (PHA) or the anti-CD3 monoclonal antibody, 12F6, to the culture of PBMCs similarly induced increased HIV replication. In this case, however, both CD4+ and CD8+ T cells were activated. No selective outgrowth of the CD4+ T cells occurred, and later in the culture the CD4+ T cell population rapidly declined.

The foregoing experiments were also performed in the presence of an effective amount of the anti-retroviral drug combination: 1 μM Zidovudine (AZT), 10 μM Didanosine (ddI), and 0.6 μM pyridnone. Addition of CD3, 8 BSMAB (1.5–3.0 μg/ml) to the culture of PBMCs isolated from HIV-infected subjects induced preferential outgrowth of the CD4+ T cells. Initially, a mild increase in virus replication occurred as indicated by a slight elevation of p24 in the culture supernatant. This was followed by rapid elimination of HIV in 9 out of 12 cultures as evidenced by absence of detectable HIV replication (measured by p24 antigen detection) and the inability of these cells to infect other cells in co-culture experiments even after the anti-retroviral drugs were removed (FIG. 5). Using the very sensitive polymerase chain reaction (PCR) technique, a very low level of HIV nucleic acid was detected in these cultures. Since no viral proteins were detected in these cultures and the treated cells did not infect co-cultured cells even with repeated stimulation, this PCR-detected HIV nucleic acid likely represents integrated incompetent viral genomic sequences that arose from mutated strains or viral genomic sequences integrated at locations where they cannot be activated to replicate.

A Single Course of CD3, 8 BSMAB, in the Presence of Anti-retroviral Drugs, Induced Proliferation of CD4+ T Cells from PBMCs of HIV-infected Subjects PBMCs ($5\times10^7$) isolated from HIV-infected subjects were placed in a hollow fiber cartridge cell culture system (CELLMAX®, Cellco, Inc.), a single course of CD3, 8 BSMAB was added for 4 days. The cultures were periodically assessed over a period of just over 200 days. Throughout this period there was a continuous expansion of CD4+ T cells. Taking into account fractionation of cultures to prevent overgrowth, after between 50 to 200 days, approximately $10^{10}$ cells to $>10^{17}$ cells could be produced from the initial inoculum of PBMCs.

Figure 2:
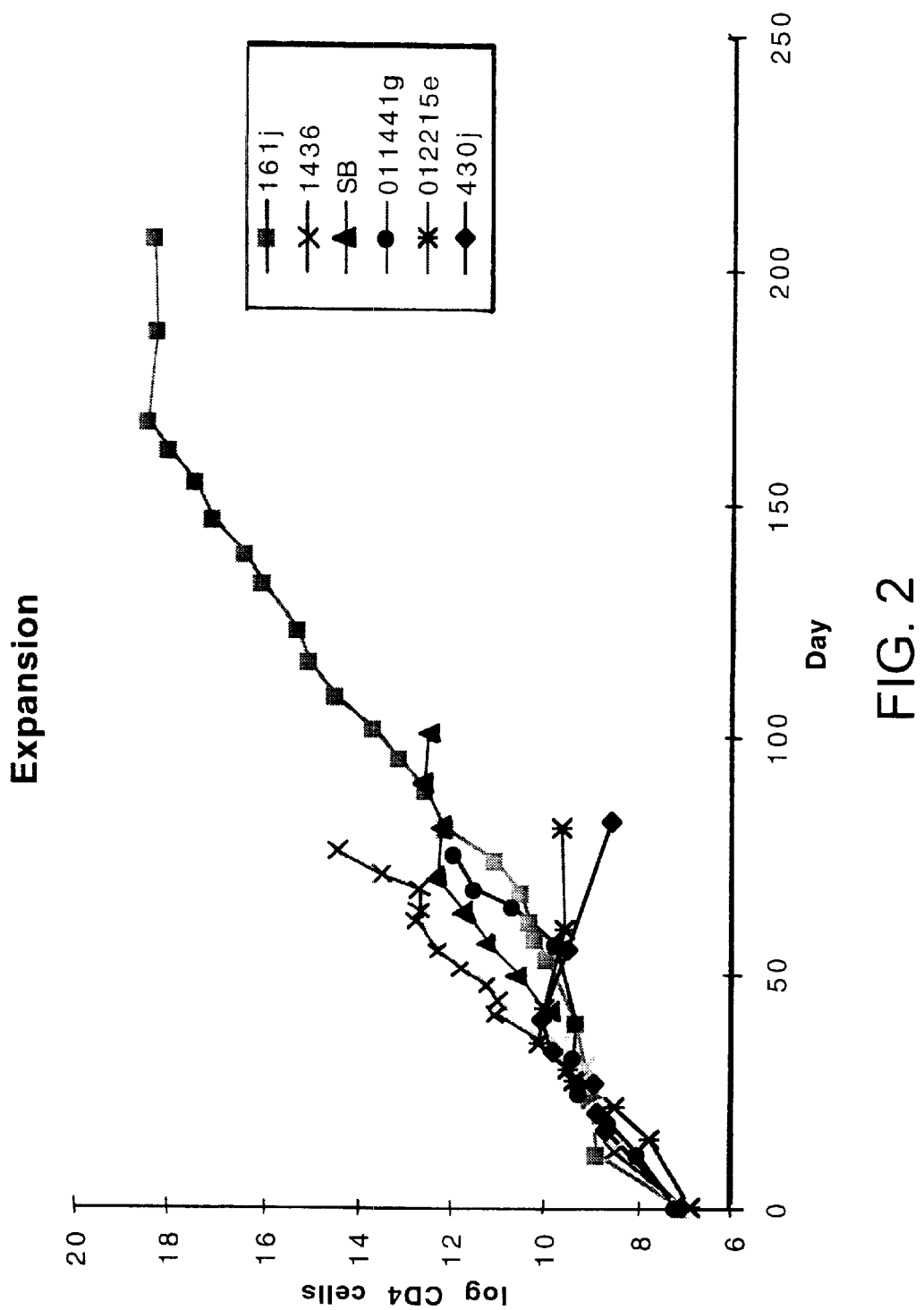
FIG. 2 is a graph depicting proliferation of CD4+ T cells induced by culturing PBMCs isolated from HIV-infected subjects in the presence of CD3, 8 BSMAB and IL-2.

We proceeded to examine whether the PBMC of HIV-1 infected subjects can also give rise to a continuously expanding CD4+ T cells in a CD3, 8 /IL-2 artificial capillary culture system. Triple anti-retroviral therapy (AZT, ddI, and nevirapine) was used for the first 19 days in culture and then replaced by fresh medium with IL-2 but without the anti-retroviral drugs. The PBMC from six HIV-1 subjects were studied to date (FIG. 4). Their growth pattern is plotted in FIG. 2.

Subject 161j is a long term nonprogressor with seroconversion 16 years ago. He is asymptomatic and has 1400 CD4+ T cell counts (Table I). Starting with $10^7$ cells, his CD4+ T cells expanded to $3\times10^{18}$ cells before plateauing. This represented an average expansion of $3\times10^{11}$-fold, dividing an average of 38 times for each cell, comparable to those of non-infected subjects. There was no detectable p24 production. Subject 1436 g had a circulating CD4+ T cell count of 350/µl and was asymptomatic at the time of testing. In the presence of CD3, 8 BS,AB for four days and triple anti-retroviral therapy for 19 days, his PBMC culture similarly rapidly became predominantly CD4+ (95%) and expanded exponentially, reaching $3\times10^{14}$ cells by the 80th day in culture. This represented an expansion of $3\times10^7$ fold (an average of 25 divisions) when the culture was arbitrarily stopped while still expanding exponentially.

Transfer of part of the harvested cells at the $10^{12}$ stage of expansion to a new cartridge resulted in a quick re-establishment of growth in a pattern that paralleled the parent cartridge after a 10 day lag period. This demonstrated that the theoretical total expansion is achievable if all the harvested cells are placed into new cartridges. The p24 level was low by the first week and declined progressively over the next 30 days. The small amount of p24 detected likely represented dilution of the initial production as the level declined to below detectable levels in the absence of further anti-retroviral therapy. Parallel CD3, 8 BSMAB/IL-2 treated cultures in the absence of anti-retroviral therapy produced rapid p24 production.

Figure 3:
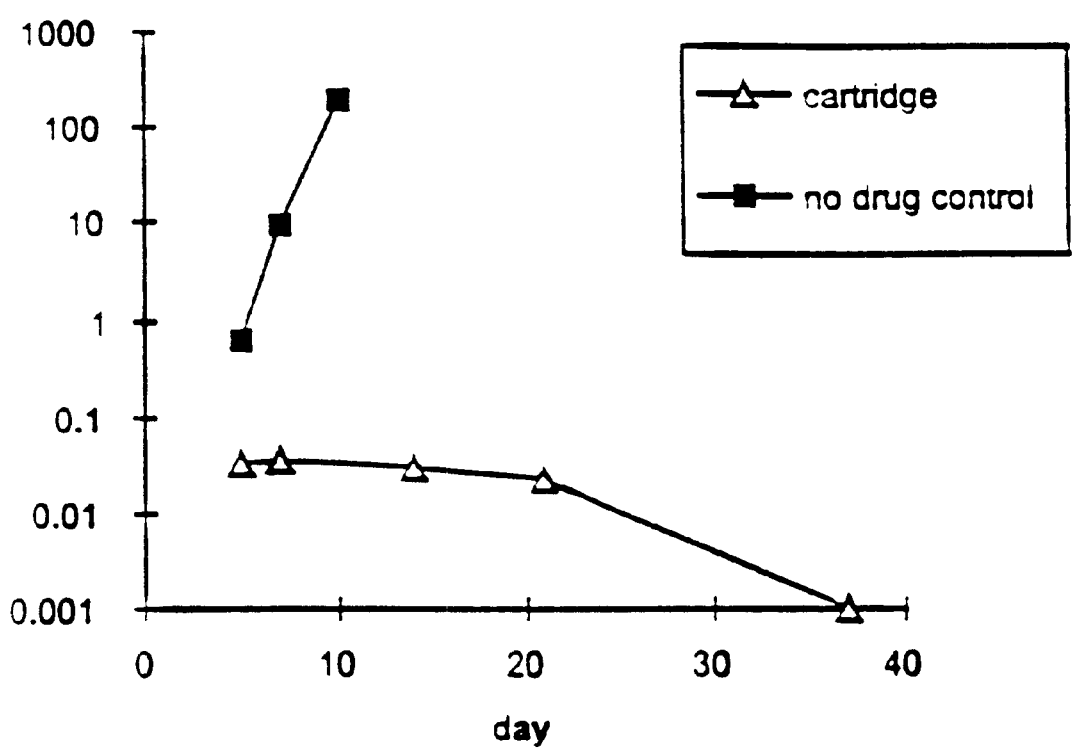
FIG. 3 is a graph depicting the rapid increase in HIV production when CD4+ T cells are cultured with CD3, 8 BSMAB and IL-2 in the absence of retroviral drugs.

Subject 011441g's peripheral CD4+ T cell count was 400/µl at the start of the culture. His PBMC culture also rapidly became predominantly CD4+ T cells. There was a slight delay in the early phase of growth, but the culture eventually reached exponential growth. The culture was stopped at $10^{12}$ cells arbitrarily by the 75th day of culture while the cells were still in exponential growth ($10^5$ fold expansion and an average of 16.7 divisions per cell). Harvested cells that were transferred picked up a growth rate that paralleled the original culture. The p24 production was low by the first week and continued to decline over the next 30 days in similar pattern to the other. Subject SB had a peripheral CD4+ T cell count of 300 at the time of the culture. His PBMC gave rise to $10^{12}$ cells ($10^5$ fold expansion and an average of 16.8 divisions per cell) by the 60th day and then plateaued between the 60–90th day. Subject 012215e's peripheral CD4+ T cell count was also 300/µl. His culture took off rapidly but then plateaued by the 30th day at only $2.2\times10^{10}$ cells ($4\times10^3$ fold expansion and an average of 12 divisions per cell). This early plateau and limited expansion was not due to viral production as the p24 production was low and declined gradually in similar fashion to the CD4+ T cell cultures of the other subjects (FIG. 3). The transferred cells likewise plateaued at an early point and paralleled the rate of growth of the parent culture.

The results presented in FIG. 3 demonstrate the rapid increase in HIV production when the CD4+ T cells were stimulated by CD3, 8+IL-2 in the absence of anti-retroviral drugs. The results presented in this figure also demonstrate that the virus reproduced at a constant low level for several weeks followed by a decline to undetectable level when the CD4+ T cells were stimulated by CD3, 8+IL-2 in the presence of effective anti-retroviral drug combination. No virus replication was detectable even after the anti-retroviral drugs were removed, utilizing an ultrasensitive RNA PCR that can detect down to 40 copies per cc.

Subject 011430j had a CD4+ T cell count of 170/µl at the start of the culture. His CD4+ T cells showed the same initial rapid expansion to $10^{10}$ cells ($10^3$ fold expansion and an average of 10 divisions per cell) by the 40th day but then rapidly declined.

In this experiment, no restimulation was used after the initial round of expansion. However, the expanded, virus free CD4+ T cells can be further expanded with additional round of stimulation in the presence of fresh accessory cells.

Importantly, the expanded CD4+ T cells were free of competent HIV. Since the total number of CD4+ T cells in the human body is approximately $10^{11}$–$10^{12}$, these experiments demonstrated that one can obtain more than enough number of CD4+ T lymphocytes to completely replace CD4+ T lymphocytes in the body with reserve for further expansion, starting with a relatively small amount of peripheral blood mononuclear cells (including CD4+ T lymphocytes).

In one experiment performed using the above protocol, PBMCs were isolated from three non-HIV infected subjects (Subjects A, B, and C) and then incubated with CD3, 8 BSMAB and IL-2 in the artificial capillary culture cartridge. After 4 days, medium was exchanged with fresh medium containing IL-2 and CD3, 8 BSMAB. With periodic replacement of the medium, the cells divided rapidly. When the culture contained between $1–2\times10^9$ cells, ¾ to ⅞ of the cells were harvested. The cells remaining in the cartridge continued to grow rapidly and each culture could be harvested repeatedly. The harvested cells were analyzed and frozen periodically.

The proliferation of T cells in cultures of PBMC from three Subjects A, B, and C are illustrated in FIG. 1. The CD4+ T cells from subject A expanded steadily in response to a single stimulation by CD3, 8 BSMAB, giving rise to $10^{19}$ cells by the 78th day of culture. The culture was stopped arbitrarily at that point, while the cells were still in exponential phase of growth. Similarly, the CD4+ T cells from subject B also expanded exponentially to about $10^{15}$ cells, when the culture was arbitrarily stopped. In comparison, the CD4+ T cells from subject C expanded to $10^{13}$ cells, plateaued, and then gradually declined.

Microscopic examination of the cells harvested throughout the different periods of culture all showed the elongated shapes typical of T cell blasts. By flow cytometry, all the cultures rapidly become 94–98% CD4+ T cells without detectable CD8+ T cells. In the early to mid phases of expansion, approximately half the cells express predominantly CD45RA and the other half express predominantly CD45RO. In the late phase of expansion, there was a gradual shift toward CD45RO expression in some cultures. This shift occurred at a much later stage of expansion than is expected from the literature, where the shift toward the "memory" phenotype (CD45RO) is reported to occur soon after mitogen-induced expansion. The CD4+ T cells expressed a high level of the IL-2Rα chain (CD25) throughout the culture, consistent with maintenance of activated status with responsiveness to IL-2. When pulsed with $^3$H-thymidine, the CD4+ T cells harvested throughout the different phases of expansion showed high level of DNA synthesis. These cells were not permanently transformed as they died when placed in standard culture flasks for several weeks in the presence of IL-2 (death occurred more quickly if IL-2 was withdrawn). The lack of transformation is further supported by the eventual decline in division of the cells of subject C even when maintained optimally in the artificial capillary culture cartridge. By flow cytometry, 0.2–2.0% of the harvested cells throughout the different phases were CD4+ CD3–, a phenotype suggestive of macrophage/monocytes/dendritic cells. This observation is consistent with the rare adherent cells with pseudopods that were seen in some harvests.

Activation of HIV Renders the Virus Susceptible to Antiretroviral Therapy

Since AZT, ddI, pyridinone, and the like inhibit HIV replication by blocking reverse transcription of HIV RNA, they are not effective in eliminating latent integrated virus from infected cells. Hence, elimination of competent HIV from the cultures indicated that the latently infected cells were in fact killed, most likely by the actively replicating virus. The small transient rise in the p24 antigen, observed early in the culture, likely reflected this initial replication. The presence of the anti-retroviral combination therapy prevented the newly released virus from taking hold in the expanded CD4+ T cells. Hence, the success of these drug combinations is dependent on the activation of the latent virus to eliminate the virus.

Activation of T cells Eliminates HIV from CD4+ T Lymphocytes and Monocytes.

In these experiments, peripheral blood mononuclear cells (PBMC) from HIV-infected subjects were used. PBMC not only have various lymphocytes subsets (CD4+, CD8+, etc.), they also contain substantial number of monocytes and dendritic cells. Elimination of HIV from the above cultures demonstrated that HIV was eliminated from monocytes and dendritic cells as well as in T cells. This elimination of HIV in monocytes and dendritic cells was not due to dying off of monocytes as the hollow fiber cartridge cultures continue to contain small amount of monocytes even in late culture. Since CD3, 8 BSMAB bind to and activate T cells rather monocytes and dendritic cells, perhaps the activated T cells secrete cytokines such as TNF-α and IFN-γ which in turn activate the HIV replication cycle in latently-infected monocytes and dendritic cells.

Similar procedures can be modified to treat patients infected with HTLV, herpesvirus family (EBV, CMV, HSV, HHV, HZV), hepatitis (hepatitis B, hepatitis C, delta agent, hepatitis E), mycobacteria (*M. tuberculosis* and *M. leprae*), and other infections with latent phase.

What is claimed is:

1. A method of treating a patient infected with HIV, the method comprising administering to the patient:
    (a) an amount of a lymphokine or a cytokine that is sufficient to induce activation of CD4+ T cells and replication of HIV within latently infected CD4+ T cells; and
    (b) a therapeutically effective amount of an anti-retroviral drug.

2. The method of claim 1, wherein the lymphokine is IL-2.

3. The method of claim 1 wherein the cytokine is TNF-α.

4. The method of claim 1 further comprising administering to the patient:
    (c) an amount of an antibody having specificity for CD3 that is sufficient to induce activation of CD4+ T cells and replication of HIV within latently infected CD4+ T cells.

5. The method of claim 1 wherein the anti-retroviral drug is a reverse transcriptase inhibitor.

6. The method of claim 1 wherein the anti-retroviral drug is selected from the group consisting of: AZT, ddI, pyridinone, lamivudine, and indinavir.

7. A method of treating a patient infected with a retrovirus, comprising administering to said patient:
    (a) an amount of a lymphokine or a cytokine that is sufficient to induce activation of cells latently infected with the retrovirus and replication of the retrovirus within latently infected cells; and
    (b) a therapeutically effective amount of an anti-retroviral drug.

* * * * *